United States Patent [19]

Markwell et al.

[11] Patent Number: 4,837,238

[45] Date of Patent: * Jun. 6, 1989

[54] PHARMACOLOGICALLY USEFUL PYRAZOLOPYRIDINES

[75] Inventors: Roger E. Markwell, Great Dunmow; Ian Hughes, Sawbridgeworth; Robert W. Ward, Old Harlow, all of England

[73] Assignee: Beecham Group p.l.c., Brentford, England

[*] Notice: The portion of the term of this patent subsequent to Dec. 17, 2002 has been disclaimed.

[21] Appl. No.: 112,050

[22] Filed: Oct. 21, 1987

Related U.S. Application Data

[63] Continuation of Ser. No. 831,166, Feb. 20, 1986, abandoned.

[30] Foreign Application Priority Data

Feb. 22, 1985 [GB] United Kingdom ............... 8504682
Oct. 1, 1985 [GB] United Kingdom ............... 8524117

[51] Int. Cl.$^4$ ............... C07D 471/04; C07D 471/14; A61K 31/44
[52] U.S. Cl. ............... 514/212; 514/293; 514/303; 540/597; 546/82; 546/119; 546/120
[58] Field of Search ............... 546/119, 120, 82; 540/597; 514/212, 303, 293

[56] References Cited

U.S. PATENT DOCUMENTS

| | | | |
|---|---|---|---|
| 3,928,368 | 12/1975 | Hoehn et al. | 546/119 |
| 4,003,908 | 1/1977 | Denzel et al. | 546/118 |
| 4,559,348 | 12/1985 | Hurst et al. | 546/119 |
| 4,576,952 | 3/1986 | Hurst et al. | 546/119 |
| 4,621,089 | 11/1986 | Ward et al. | 514/303 |

FOREIGN PATENT DOCUMENTS

| | | |
|---|---|---|
| 0119774 | 9/1984 | European Pat. Off. |
| 2301268 | 8/1973 | Fed. Rep. of Germany |
| 2139035 | 1/1973 | France |
| 2164866 | 8/1973 | France |
| 2299867 | 9/1976 | France |

OTHER PUBLICATIONS

Foster et al., J. C. S. Perkin, Trans., 1, p. 507–12, (1976).
Derwent Abstract 56578Y/32.
Chemical Abstract, Abstract CA87(21):168030e.
Ajello, *Journal of Heterocyclic Chemistry*, 8, (6), 1035–1037, (1971).

*Primary Examiner*—Mary C. Lee
*Assistant Examiner*—Bernard I. Dentz
*Attorney, Agent, or Firm*—James F. Haley, Jr.; David K. Barr

[57] ABSTRACT

Compounds of the formula (I):

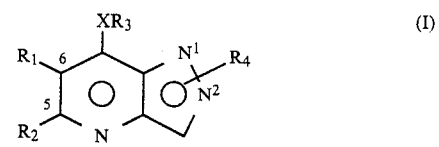

wherein:

X is NR wherein R is hydrogen, $C_{1-6}$ alkyl; oxygen; sulphur; SO; or $SO_2$; or R and $R_3$ taken together are $C_{4-6}$ polymethylene;

$R_1$ is hydrogen or $C_{1-6}$ alkyl; and $R_2$ is CN, $CR_5R_6Y$ where $R_5$ and $R_6$ are independently selected from hydrogen and $C_{1-4}$ alkyl and Y is selected from hydrogen, $OR_7$ or $SR_7$ where $R_7$ is hydrogen, $C_{1-4}$ alkyl, $C_{2-4}$ alkanoyl, and $NR_8R_9$ where $R_8$ and $R_9$ are independently hydrogen, $C_{1-4}$ alkyl, $C_{2-4}$ alkenyl or $C_{2-4}$ alkanoyl or $R_8$ and $R_9$ together are $C_{4-6}$ polymethylene, or $COR_{10}$ where $R_{10}$ is $C_{1-4}$ alkyl, provided that Y is other than hydrogen when $R_1$ is hydrogen;

or $R_2$ is hydrogen $C_{1-6}$ alkyl or phenyl optionally substituted by halogen, $CF_3$, $C_{1-4}$ alkoxy or $C_{1-4}$ alkyl; and $R_1$ is CN, $CR_5R_6Y$ or $COR_{10}$ as defined for $R_2$ above;

or $R_1$ and $R_2$ together form $C_3-C_6$ polymethylene optionally substituted by $C_1-C_4$ alkyl;

$R_3$ is $C_{1-10}$ alkyl or $C_{3-10}$ cycloalkyl, either optionally substituted by hydroxy, $C_{1-4}$ alkoxy, thiol, $C_{1-4}$ alkylthio or $NR_{11}R_{12}$ wherein $R_{11}$ and $R_{12}$ are independently hydrogen, $C_{1-6}$ alkyl or $C_{2-7}$ alkanoyl or together are $C_{3-6}$ polymethylene; $C_{2-10}$ alkenyl; or phenyl optionally substituted by one or two of halogen, $CF_3$, $C_{1-4}$ alkoxy, $C_{1-4}$ alkyl, hydroxy, nitro, cyano, $C_{2-10}$ acyloxy, $NR_{13}R_{14}$ wherein $R_{13}$ and $R_{14}$ are independently selected from hydrogen, $C_{1-6}$ alkyl, $C_{2-7}$ alkanoyl, $C_{1-6}$ alkylsulphonyl or $COR_{15}$ wherein $R_{15}$ is hydroxy, $C_{1-6}$ alkoxy or $NR_{16}R_{17}$ wherein $R_{16}$ and $R_{17}$ are independently selected from hydrogen or $C_{1-6}$ alkyl; or together with R is $C_{4-6}$ polymethylene; and $R_4$ is hydrogen; or $C_{1-4}$ alkyl or benzyl optionally substituted in the phenyl ring by one or two of halogen, $CF_3$, $C_{1-4}$ alkoxy or $C_{1-4}$ alkyl and is attached at nitrogen atom 1 or 2, are disclosed as having utility in the treatment of inflammatory and allergic disorders.

9 Claims, No Drawings

PHARMACOLOGICALLY USEFUL PYRAZOLOPYRIDINES

This is a continuation, of application Ser. No. 831,166, filed Feb. 20, 1986 now abandoned, entitled NOVEL COMPOUNDS.

The present invention relates to pyrazolopyridines having useful pharmacological activity, to a process for their preparation and to their use as pharmaceuticals.

European Patent Publication No. 119774 discloses a group of pyrazolopyridine derivatives which are described as of potential use as anti-inflammatories.

A structurally distinct group of pyrazolopyridine derivatives have now been discovered which compounds have anti-inflammatory (including anti-rheumatic) and/or anti-allergy activity.

Accordingly, the present invention provides a compound of the formula (I) and pharmaceutically acceptable salts and solvates thereof:

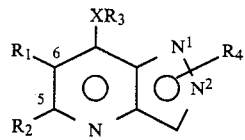

wherein:

X is NR wherein R is hydrogen; $C_{1-6}$ alkyl; oxygen; sulphur; SO; or $SO_2$; or R and $R_3$ taken together are $C_{4-6}$ polymethylene;

$R_1$ is hydrogen or $C_{1-6}$ alkyl; and $R_2$ is CN, $CR_5R_6Y$ where $R_5$ and $R_6$ are independently selected from hydrogen and $C_{1-4}$ alkyl and Y is selected from hydrogen, $OR_7$, $SR_7$ where $R^7$ is hydrogen, $C_{1-4}$ alkyl or $C_{2-4}$ alkanoyl, and $NR_8R_9$ where $R_8$ and $R_9$ are independently hydrogen, $C_{1-4}$ alkyl, $C_{2-4}$ alkenyl or $C_{2-4}$ alkanoyl or $R_8$ and $R_9$ together are $C_{4-6}$ polymethylene, or $R_2$ is $COR_{10}$ where $R_{10}$ is $C_{1-4}$ alkyl, provided that Y is other than hydrogen when $R_1$ is hydrogen;

or $R_2$ is hydrogen, $C_{1-6}$ alkyl or phenyl optionally substituted by halogen (e.g., fluorine, chlorine, bromine or iodine), $CF_3$, $C_{1-4}$ alkoxy or $C_{1-4}$ alkyl; and $R_1$ is CN, $CR_5R_6Y$ or $COR_{10}$ as defined for $R_2$ above;

or $R_1$ and $R_2$ together form $C_3-C_6$ polymethylene optionally substituted by $C_1-C_4$ alkyl;

$R_3$ is $C_{1-10}$ alkyl or $C_{3-10}$ cycloalkyl, either optionally substituted by hydroxy, $C_{1-4}$ alkoxy, thiol, $C_{1-4}$ alkylthio or $NR_{11}R_{12}$ wherein $R_{11}$ and $R_{12}$ are independently hydrogen, $C_{1-6}$ alkyl or $C_{2-7}$ alkanoyl or together are $C_{3-6}$ polymethylene; $C_{2-10}$ alkenyl; or phenyl optionally substituted by one or two of halogen, $CF_3$, $C_{1-4}$ alkoxy, $C_{1-4}$ alkyl, hydroxy, nitro, cyano, $C_{2-10}$ acyloxy, $NR_{13}R_{14}$ wherein $R_{13}$ and $R_{14}$ are independently selected from hydrogen, $C_{1-6}$ alkyl, $C_{2-7}$ alkanoyl or $C_{1-6}$ alkylsulphonyl or $COR_{15}$ wherein $R_{15}$ is hydroxy, $C_{1-6}$ alkoxy or $NR_{16}R_{17}$ wherein $R_{16}$ and $R_{17}$ are independently selected from hydrogen or $C_{1-6}$ alkyl; or together with R is $C_{4-6}$ polymethylene; and $R_4$ is hydrogen; or $C_{1-4}$ alkyl or benzyl optionally substituted in the phenyl ring by one or two of halogen, $CF_3$, $C_{1-4}$ alkoxy or $C_{1-4}$ alkyl and is attached at nitrogen atom 1 or 2.

Suitable values for X include those wherein R in NR is hydrogen, methyl, ethyl, n- and iso-propyl, preferably hydrogen; and oxygen or sulphur. Favourably X is NH.

Suitable values for $R_1/R_2$ include hydrogen, methyl, ethyl, n- and iso-propyl, aminomethyl optionally N-substituted, acetamidomethyl and acetyl, or together forming $C_3$ or $C_4$ polymethylene.

Suitable values for $R_3$ include methyl, ethyl, n- and iso-propyl, n-, iso- sec- and tert-butyl, n-pentyl, $(CH_2)_nCH_3$ wherein n is 4 to 7, or cyclohexyl, optionally substituted by methyl, ethyl and/or hydroxy, methoxy, n- or iso-propoxy, thio, methylthio or amino optionally substituted by one or two methyl or acetyl groups or by $C_4$ or $C_5$ polymethylene; vinyl, prop-1-enyl, prop-2-enyl, 1-methylvinyl, but-1-enyl, but-2-enyl, but-3-enyl, 1-methylenepropyl, 1-methylprop-1-enyl and 1-methylprop-2-enyl in their E and Z forms where stereoisomerism exists; or phenyl optionally substituted by one or two chloro, bromo, methoxy, ethoxy, n- and iso-propoxy, methyl, ethyl, n- and iso-propyl, n-, iso-, sec- and tert-butyl, hydroxy, nitro, cyano, acetoxy, propionyloxy, benzyloxy, $NR_{13}{}^1R_{14}{}^1$ wherein $R_{13}{}^1$ and $R_{14}{}^1$ are independently selected from hydrogen, methyl, ethyl, n- and iso-propyl, acetyl, propionyl, methylsulphonyl and ethylsulphonyl; $COR_{15}{}^1$ wherein $R_{15}{}^1$ is hydroxy, methoxy, ethoxy or $NR_{16}{}^1R_{17}{}^1$ wherein $R_{16}{}^1$ and $R_{17}{}^1$ are independently selected from hydrogen, methyl, n- and iso-propyl. Preferred values for $R_3$ include n-butyl, n-pentyl, allyl, prop-2-enyl, 2-methylallyl, 2-hydroxyethyl, 3-hydroxypropyl, 2-dimethylaminoethyl, 3-dimethylaminopropyl, 3-diethylaminopropyl, phenyl and phenyl substituted by one of hydroxy, nitro, cyano, carboxy, t-butyl and ethoxycarbonyl in the 3- or 4-position. More preferred values for $R_3$ include n-butyl, prop-2-enyl and 2-hydroxyethyl, 3-dimethylaminopropyl and 3-diethylaminopropyl.

Suitable values for $R_4$ include hydrogen, methyl, ethyl, n- and iso-propyl and benzyl. Preferably, $R_4$ is hydrogen or 2-methyl. More preferably, $R_4$ is hydrogen.

It will be appreciated that when $R_4$ is hydrogen the compounds of formula (I) exist as tautomers, i.e. the $R_4$ hydrogen atom is labile. The compounds wherein $R_4$ is hydrogen are therefore of formulae (IIa) and (IIb).

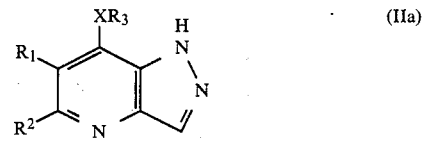

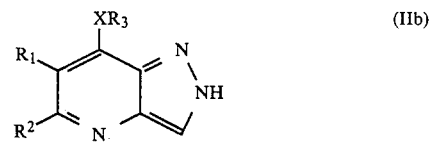

The compounds of the formula (I) can form acid addition salts with acids, such as the conventional pharmaceutically acceptable acids, for example hydrochloric, hydrobromic, phosphoric, acetic, fumaric, salicylic, citric, lactic, mandelic, tartaric and methanesulphonic. Such compounds form part of the present invention, as do solvates, for example hydrates, of the compounds of formula (I) or salts thereof.

There is a group of compounds within formula (I) wherein $R_1$ is hydrogen or $C_{1-6}$ alkyl; and $R_2$ is CN, $CR_5R_6Y'$ wherein $Y'$ is $OR_7$, $SR_7$ or $NR_8R_9$, or $COR_{10}$; or $R_2$ is hydrogen, $C_{1-6}$ alkyl or phenyl optionally substituted as defined in formula (I); and $R_1$ is CN, $CR_5R_6Y$ or $COR_{10}$; and wherein Y, $R_5$, $R_6$, $R_7$, $R_8$, $R_9$, $R_{10}$ and the remaining variables are as defined for formula (I).

There is a further group of compounds within formula (I) wherein either $R_1$ is hydrogen and $R_2$ is CN, $COR_{10}$ or $CR_5R_6Y'$ or $R_1$ is CN, $COR_{10}$ or $CR_5R_6Y$ and $R_2$ is hydrogen, and the remaining variables are as defined for formula (I).

$R_4$ when other than hydrogen is preferably attached at nitrogen atom 2.

There is a preferred group of compounds within formula (I) of formula (III):

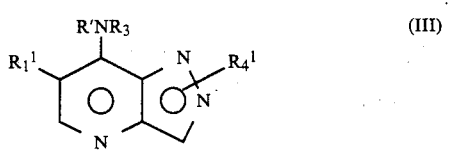

wherein $R_1{}^1$ is CN, $COR_{10}$ or $CR_5R_6Y$, R' is hydrogen or methyl, $R_4{}^1$ is hydrogen or 2-methyl, and $R_3$, $R_{10}$, $R_5$, $R_6$ and Y are as defined for formula (I).

Suitable and preferred values for $R_1{}^1$, R', $R_4{}^1$ and $R_3$ are as described for the relevant variables under formula (I).

Another sub-group of compounds within formula (III) is of formula (IV):

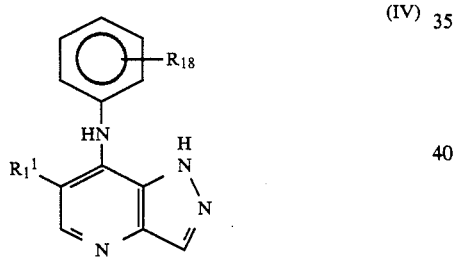

wherein $R_{18}$ is hydrogen, chloro, bromo, methoxy, ethoxy, hydroxy, cyano, carboxyl, ethoxycarbonyl, nitro or t-butyl.

Preferably $R_{18}$ when other than hydrogen is attached at the 3- or 4-position, most preferably the 4-position.

A preferred sub-group of compounds within formula (III) is of formula (V):

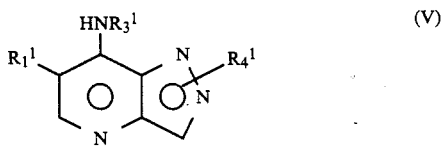

wherein $R_3{}^1$ is n-butyl, iso-butyl, allyl, 2-hydroxyethyl, 3-dimethylaminopropyl, or 3-diethylaminopropyl, and $R_1{}^1$ and $R_4{}^1$ are as defined in formula (III).

Suitable and preferred values for the variables are as described for the respective variables under formula (I).

A further group of compounds within formula (I) is of formula (VI):

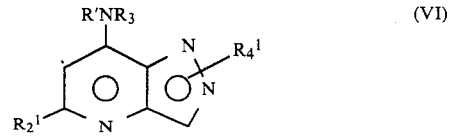

wherein $R_2{}^1$ is CN, $CR_5R_6Y'$ or $COR_{10}$ as defined and the remaining variables are as defined for formula (III).

Suitable and preferred values for $R_2{}^1$, R', $R_3$ and $R_4{}^1$ are as described for the relevant variables under formula (I).

A preferred sub-group of compounds within formula (VI) is of formula (VII):

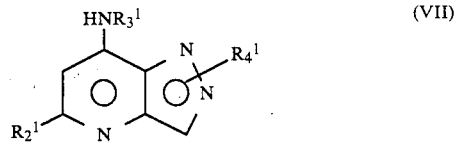

wherein $R_3{}^1$ and $R_4{}^1$ are as defined for formula (V) and $R_2{}^1$ is as defined for formula (VI).

Suitable and preferred values for the variables are as described for the relevant variables under formula (I).

Another sub-group of compounds within formula (I) is of formula (VIII):

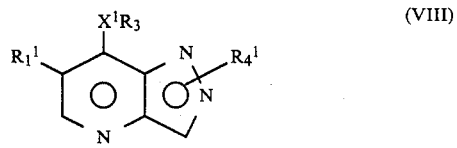

wherein $X^1$ is oxygen or sulphur, and $R_1{}^1$, $R_3$ and $R_4{}^1$ are as defined for formula (III).

Suitable and preferred values for $X^1$, $R_1{}^1$, $R_3$ and $R_4{}^1$ are as described for the relevant variables under formula (I).

Another group of compounds within formula (I) is of formula (IX):

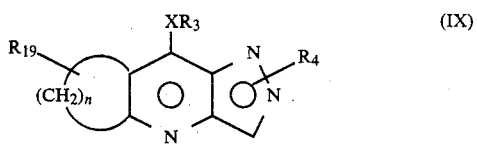

in which n is 3 to 8 and $R_{19}$ is hydrogen or $C_1$–$C_4$ alkyl, and X, $R_3$ and $R_4$ are as defined for formula (I)

A preferred sub-group of compounds within formula (X) is of formula (X):

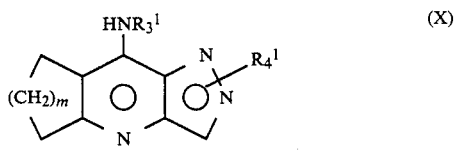

in which $R_3{}^1$ and $R_4{}^1$ are as defined for formula (V) and m is 1 or 2.

Suitable and preferred values for the variables in formulae (IX) and (X) are as described for formula (I).

The present invention also provides a process for the preparation of a compound of formula (I) or a pharmaceutically acceptable salt or solvate thereof, which process comprises the reaction of a compound of formula (XI):

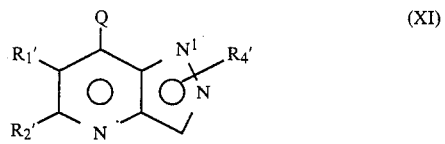

wherein Q is a leaving group, $R_1'$ and $R_2'$ are $R_1$ and $R_2$ as defined for formula (I) or atoms or groups convertible thereto and $R_4'$ is $R_4$ as defined for formula (I) or an atom or group convertible thereto, with a compound of formula (XII):

wherein $X^2$ is NR (as defined in formula (I)), oxygen or sulphur and $R_3'$ is $R_3$ or a group or atom convertible thereto; and thereafter optionally and as necessary converting $X^2$ to X, $R_1'$ to $R_1$, $R_2'$ to $R_2$, $R_3'$ to $R_3$ and/or $R_4'$ to $R_4$, and/or forming a pharmaceutically acceptable salt or solvate thereof.

It will be appreciated that one compound of formula (I) may be converted to another compound of formula (I) by interconversion of suitable substituents. Thus certain compounds of formula (I) are useful intermediates in forming other compounds of the present invention.

Also salts or solvates of the compounds of formula (I) which are not pharmaceutically acceptable may be useful as intermediates in the production of pharmaceutically acceptable salts or solvates. Accordingly such salts or solvates also form part of this invention.

Suitable leaving groups Q include halogens such as chloro and bromo, preferably chloro.

The reaction may be carried out under conventional conditions for nucleophilic aromatic displacements, at elevated temperatures using excess of reagent as solvent (eg aniline when X is NR) or in an inert solvent such as toluene, ethanol, dimethylformamide, dimethylsulphoxide, dioxan or water. The reaction preferably takes place in a sealed tube if $HX_2R_3'$ is of low boiling point.

Alternatively, when $X^2$ is oxygen or sulphur, the reaction may take place in the presence of a base, such as sodium hydride, potassium t-butoxide or sodium t-butoxide.

Compounds of formula (I) wherein X is SO or $SO_2$ may be prepared from the corresponding compounds wherein X is S by conventional oxidation methods, such as using sodium periodate or one equivalent of m-chloroperbenzoic acid (to form the compound of formula (I) wherein X is SO) or two equivalents of m-chloroperbenzoic acid (to form the compound of formula (I) wherein X is $SO_2$).

Conversion of an R hydrogen in X to an R $C_{1-6}$ alkyl group may be carried out by conventional amine alkylation or acylation (e.g. formylation) followed by reduction.

Conversion of $R_1'/R_2'$ to $R_1/R_2$ may be carried out by conventional functional group interchanges. Thus for example:

(i) a CN group may be provided by the dehydration of an amide group, preferably with phosphorous pentoxide.
(ii) an hydromethyl group may be provided by the reduction of an alkoxycarbonyl group, preferably with a metal hydride, such as $LiAlH_4$. In this case it is necessary to protect the pyrazole N-H with a suitable protecting group, such as 2-methoxy-2-propyl.
(iii) an alkanoyl group may be provided by the reaction of a CN group with an organo-metallic reagent such as a Grignard reagent.
(iv) a secondary alcohol group may be provided by the reduction of an alkanoyl group, preferably with a metal hydride.
(v) a tertiary alcohol group may be provided by the reaction of an alkanoyl group with an organo-metallic reagent such as a Grignard reagent.
(vi) a primary aminomethyl group may be provided by the reduction of a CN group, preferably with a metal hydride or using $PtO_2/HCl-H_2$.
(vii) an aminomethyl group may be provided by the reduction of the corresponding amide, preferably with a metal hydride.
(viii) an alkanoyloxyalkyl group may be provided by the acylation of the corresponding alcohol, preferably using the appropriate acid anhydride in trifluoroacetic acid at elevated temperatures.
(ix) an alkanoylaminoalkyl group may be provided by the acylation of the corresponding amino alkyl group, preferably using the appropriate acid anhydride under mild conditions.
(x) a methyl group in particular in the 6-position may be provided by the reduction of an alkoxycarbonyl group, preferably with lithium aluminium hydride.
(xi) an aminoalkyl group may be provided by converting the hydroxy of the corresponding alcohol to a leaving group and reacting with an appropriate amine nucleophile.
(xii) alternatively an aminoalkyl group of the formula $CH(R_5)NR_8R_9$ may be provided by the reductive amination of the corresponding keto group $COR_5$, preferably by reaction with the appropriate amine followed by hydrogenation or by reaction with the amine and sodium cyanoborohydride.
(xiii) an alkoxyalkyl group may be provided by the alkylation of the corresponding alcohol, preferably by reaction of the sodium salt of the alcohol with the appropriate alkyl iodide.
(xiv) an alkylthioalkyl group may be provided by the reaction of the corresponding derivatised hydroxyalkyl or haloalkyl group with the appropriate alkylthiol.

$R_1'$ or $R_2'$ may be methyl, in which case it may be converted to a $CO_2H$ group by conventional oxidation with an oxidising agent such as potassium permanganate. This conversion is preferably, however, carried out on the intermediate of formula (XI) or at an earlier stage.

An $CO_2H$ group in $R_1'$ or $R_2'$ may be converted to an alkoxycarbonyl group by conventional esterification procedures or to an amide group by condensation in the presence of a dehydrating agent, such as dicyclohexylcarbodiimide.

An $R_1'$ or $R_2'$ group when amide can be converted to an ester group by conventional hydrolysis/esterification in ethanolic HCl. It will be appreciated that when $R_1'$ or $R_2'$ is an ester group, reaction of the compound of formula (XII) with the compound of formula (XI) may also substitute the ester to give an amide.

Conversions of $R_3$ phenyl substituted are generally known in the art of aromatic chemistry. Examples of such conversions are as follows:

(a) an hydroxy group may be converted to acyloxy by conventional acylation procedures, preferably using the acid anhydride in trifluoroacetic acid at elevated temperature;

(b) a cyano group may be converted to carboxy by base catalysed hydrolysis; preferably using sodium hydroxide in ethanol followed by neutralisation with acid.

(c) an alkoxycarbonyl group may be converted to $CONR_{16}R_{17}$ by heating with the appropriate amine;

(d) a nitro group may be converted to an amino group by reduction, preferably by catalytic reduction using palladium on charcoal;

(e) an amino group may be converted to an alkylamino or acylamino group by conventional amine acylation or alkylation; the acylation is preferably carried out using an acid anhydride and the alkylation using the alkyl halide;

(f) an amino group may be converted to an alkylsulphonylamino group by reaction with the appropriate alkylsulphonyl chloride, preferably using an acid acceptor such as triethylamine in an inert solvent such as dichloromethane.

An $R_4$ hydrogen atom may be converted to an $R_4$ $C_{1-6}$alkyl group by conventional alkylation procedures.

It will be appreciated that these conversions may take place in any desired or necessary order. Conversions, in particular those involving amine substitution, may also substitute an $R_4$ hydrogen which therefore may need to be protected using an amine protecting group, such as para-methoxybenzyl, and subsequently removed by heating in the presence of an acid such as trifluoroacetic acid.

Pharmaceutically acceptable salts of the compounds of formula (I) may be formed conventionally by reaction with the appropriate acid, and solvates by crystallization from the appropriate solvent.

Compounds of the formula (XI) are either known compounds or can be prepared by analogy with processes for preparing structurally similar known compounds.

For example, compounds of the formula (XI) wherein Q is chloro may be prepared by the phosphorus oxychloride chlorination of a compound of formula (XIII):

(XIII)

It will be appreciated that the compounds of formula (XIII) wherein $R_4$ is hydrogen exist in the predominant tautomeric form of formula (XIIIa):

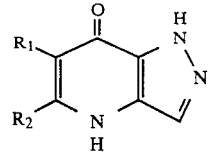

(XIIIa)

Compounds of the formula (XIII) may be prepared as described in J. Chem. Soc. Perkin Trans. I, 1976 (5), 507 or by analogous methods thereto.

In a further aspect the invention provides a pharmaceutical composition which comprises a compound of formula (I) or a pharmaceutically acceptable salt or solvate thereof and a pharmaceutically acceptable carrier.

The compositions may be adapted for administration via the topical, oral, rectal or injection routes. The compositions of this invention may be prepared by admixture of the active ingredient with the carrier, such as diluents, binder, fillers, disintegrants, flavouring agents, colouring agents, lubricants, preservatives, in conventional manner. These conventional excipients may be employed in conventional manner, for example as in the preparation of compositions of ketoprofen, indomethacin, naproxen, acetylsalicylic acid or other anti-inflammatory agents.

The compounds of the invention have topical anti-inflammatory activity and therefore will normally be made up into a composition which is a cream, lotion, liniment, gel, gel stick, ointment, spray or aerosol for topical administration to the skin.

Cream, lotion, liniment, gel, gel stick, ointment, spray and aerosol formulations that may be used for compounds of the formula (I) are conventional formulations well known in the art, for example, as described in standard text books of pharmaceutics and cosmetics, such as Harry's Cosmeticology published by Leonard Hill Books, Remington's Pharmaceutical Sciences, and the British and U.S. Pharmacopoeias. A standard emulsifying ointment base or anhydrous polyethylene glycol are simple examples of such suitable formulations.

Examples of oils suitable for inclusion in a standard emulsifying ointment base include mineral oils, vegetable oils, synthetic fatty acid esters, fatty alcohols, lanolin and its derivatives.

The compositions of the present invention will normally include a suitable emulsifier. The composition can range from liquid through semi-liquid to gel types according to the type of emulsion and quantity of any thickening agent which may be present. Examples of emulsifiers include polyhydric alcohol esters such as sorbitan monostearate, fatty acid esters such as glyceryl monostearate, and polyester derivatives of fatty acids or fatty alcohols.

The compositions may also contain anti-oxidants and other conventional ingredients such as preservatives, perfumes and alcohol. Advantageously, a penetrating agent such as AZONE may also be included.

The compositions for topical treatment may also contain other therapeutic agents such as anti-infective and/or anti-viral agents. Suitable anti-infective agents include the topically applicable antibacterial, anti-yeast, anti-fungal and anti-herpes agents.

These compositions may be used in the topical treatment of atopic and contact dermatitis, psoriases, acne, eczema and other inflammatory dermatoses and inflammatory conditions of eyes, ears, nose and throat. Treatment of inflammation of the skin may, however, also be carried out utilising an oral composition of the invention, as hereinbefore described.

It will be appreciated that the amount of compound of the formula (I) used will depend on a number of factors such as the nature and severity of the disorder being treated, and the specific compound being used. However, by way of illustration it is believed that effective therapy can be achieved using roughly similar amounts of the compounds of formula (I) as would be used of hydrocortisone. A typical formulation will suitably contain 0.1 to 20%, more suitably 0.5 to 5% of the compound of formula (I).

A composition of this invention is useful in the treatment of rheumatism and arthritis and in the treatment of pain and other inflammatory conditions and also in the treatment of the prophylaxis of bronchial asthma, rhinitis, hay fever and allergic eczema. Suitably the oral compositions of this invention will be in the form of a unit dose such as a tablet, capsule or reconstitutable powder in a sachet. For use in the treatment of rheumatism and arthritis and in the treatment of pain and other inflammatory conditions, such unit doses will generally contain from 10 mg to 1000 mg and more preferably will contain from about 30 mg to 500 mg for example 50 mg to 250 mg of active agent, for example about 50, 100, 150, 200, 250, 300, 350, 400, 450 or 500 mg. These compositions may be administered once or more times a day, for example 2, 3 or 4 times daily, so that the total daily dose for a 70 kg adult will usually be in the range of 20 to 3000 mg and more usually in the range 40 to 1000 mg. Alternatively the unit dose may contain from 2-20 mg of active agent and may be administered in multiples if desired to give the preceeding daily dose of 20 to 3000 mg.

For use in the treatment or prophylaxis of allergic disorders, with any of the formulations of the present invention, a suitable dosage unit may contain 0.01 to 500 mg of active ingredient, more suitably 1 to 500 mg for use via the oral route, 0.01 to 10 mg via inhalation, which is preferred. The effective dose of compound depends on the particular compound employed, the condition of the patient and the frequency and route of administration, but in general is in the range of from 0.001 mg/day to 100 mg/day per kilogram of the patient's body weight, in single or divided doses.

No adverse toxicological effects are indicated at any of the aforementioned dosage ranges.

Where appropriate, small amounts of other anti-asthmatics and bronchodilators, for example sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included. A favoured form of oral composition of this invention is a tablet containing the active agent. The active agent may be in the form of a recompressed granulate of the active ingredient in intimate mixture with a lubricant such as magnesium stearate, a filler such as microcrystalline cellulose and a disintegrant such as sodium starch glycollate.

A particular composition of the invention for inflammatory diseases is a hard gelatin capsule containing the required amount of a compound of the invention in the form of a powder or granulate in intimate mixture with a lubricant, such as magnesium stearate, a filler, such as microcrystalline cellulose, and a disintegrant, such as sodium starch glycollate.

Preparations especially suitable for administration to the respiratory tract include, for example, a snuff, an aerosol, a solution for a nebulizer, or a microfine powder for insufflation, alone or in combination with an inert carrier such as lactose. In such a case the particles of active compound suitably have diameters of less than 50 microns, preferably less than 10 microns.

For parenteral administration, fluid unit dosage forms are prepared utilising a compound of the formula (I) or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle.

Parenteral suspensions are prepared in substantially the same manner, except that the compound is suspended in the vehicle instead of being dissolved and sterilised by exposure to ethylene oxide before suspension in a sterile vehicle. Advantageously, a surfactant or wetting agent is included in the composition to facilitate uniform distribution of the compound.

The invention further provides a method of treatment or prophylaxis of inflammatory and/or allergic conditions in mammals including man which comprises the administration of a compound of formula (I) or a pharmaceutically acceptable salt or solvate thereof to the sufferer.

The invention also provides a compound of formula (I) or a pharmaceutically acceptable salt or solvate thereof for use in treating disorders in mammals, and in particular inflammatory and/or allergic conditions.

The invention also provides the use of a compound of formula (I) or a pharmaceutically acceptable salt or solvate thereof for use in the manufacture of a medicament for treating inflammatory and/or allergic conditions.

Mammals which may be thus treated include humans and domestic animals such as dogs, cats or horses.

Most suitably the medicament will be administered orally as 1, 3 or 4 doses per day at the dose level previously indicated.

The following Examples illustrate compounds of the invention, and the Descriptions illustrate the preparation of intermediates.

DESCRIPTION 1

Ethyl 7-chloro-1H-pyrazolo[4,3-b]pyridine-6-carboxylate

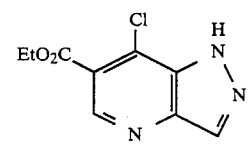

A solution of ethyl 4,7-dihydro-7-oxo-1H-pyrazolo[4,3-b]pyridine-6-carboxylate[1] in phosphorus oxychloride was heated under reflux for 45 min. After removing excess reagent in vacuo, the residue was made basic with saturated sodium hydrogen carbonate solution. The precipitated solid was washed with water, then extracted with ethyl acetate to give the crude title compound.

δ(DMSO d₆)
1.4 (3H, t, J=7 Hz)
4.3 (2H, q, J=7 Hz)
8.4 (1H, s) 8.8(1H, s)

[1]. H. E. Foster and J. Hurst, J. Chem. Soc., Perkin Trans. 1, 1976, 507

A much improved yield (67%) of the title compound was obtained by maintaining the reaction mixture at 70°-80° C. rather than at reflux temperature.

DESCRIPTION 2

Ethyl 7-Allylamino-1H-pyrazolo[4,3-b]-pyridine-6-carboxylate

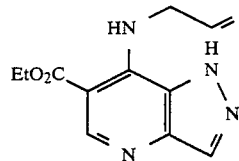

Ethyl 7-chloro-1H-pyrazolo[4,3-b]pyridine-6-carboxylate (2.25 g, 0.01 mole) and allylamine (20 ml) were stirred together overnight at room temperature. The excess allylamine was removed under reduced pressure. The residue was dissolved in the minimum volume of aqueous ethanol and sufficient 10% sodium carbonate added to give pH 8.

The resulting solid was collected and dried to give a yellow solid, which was recrystallized from ether-pentane with a few drops of methanol to facilitate solubility, to give the title compound as the free base (1.0 g, 42%) m.p. 218°-222° C. (Found: C, 58.32; H, 5.72; N, 22.85. $C_{12}H_{14}N_4O_2$ requires C, 58.53; H, 5.73; N, 22.75%)

δ(CDCl₃)
1.4 (3H, t, J=7 Hz)
4.3 (2H, q, J=7 Hz)
4.7-4.85 (2H, m)
5.05-5.5 (2H, m)
5.75-6.41 (1H, m)
8.15 (1H, s)
8.8 (1H, s)

DESCRIPTION 3

7-Allylamino-1H-pyrazolo[4,3-b]pyridine-6-carboxylic acid (D3)

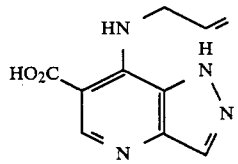

Ethyl 7-allylamino-1H-pyrazolo[4,3-b]pyridine-6-carboxylate (5.0 g, 20 mmol) was added to a solution of sodium hydroxide (2.4 g, 60 mmol) in water (100 ml) and heated under reflux for 60 min. The solution was filtered, diluted with water (200 ml) and made neutral with 5N hydrochloric acid. The solid was filtered off, washed with water and dried to give the title compound (4.25 g, 96%), m.p. 240°-242° C.

δ (DMSOd₆/TFA):
0.92 (3H, t, J 7 Hz)
1.1-1.80 (4H, m)
4.20 (1H, m)
8.55 (1H, s)
8.85 (1H, s)

DESCRIPTION 4

7-Allylamino-1H-pyrazolo[4,3-b]pyridine-6-carboxamide (D4)

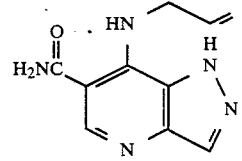

A mixture of 7-allylamino-1H-pyrazolo[4,3-b]pyridine-6-carboxylic acid (3.8 g, 17.4 mmol) and thionyl chloride (10 ml) was heated at reflux for 10 min. Excess thionyl chloride was removed in vacuo, and the residual solid was added, with stirring to an ice-cooled solution of 0.880 ammonia (20 ml) in water (10 ml). The mixture was shaken well, then made strongly basic with 40% sodium hydroxide solution. The pH was adjusted back to pH 8 with 5N hydrochloric acid, and the product was extracted into ethyl acetate. The extracts were washed with brine, then dried (MgSO₄) and evaporated in vacuo. The residual solid was recrystallised from THF/ethanol/pentane to give the title compound as yellow needles (1.81 g, 48%), m.p. 254°-258° C. Found: C, 55.41; H, 5.13; N, 31.83; $C_{10}H_{11}N_5O$ requires C, 55.29; H, 5.10; N, 32.24%

δ (DMSO d₆):
4.60 (2H, br t)
5.05-5.40 (2H, m)
5.60-6.30 (1H, m)
7.55 (2H, br s, exchanged with D₂O)
8.25 (1H, s)
8.57 (1H, s)
9.95 (1H, br t, exchanged with D₂O)
13.70 (1H, br s, exchanged with D₂O)

DESCRIPTION 5

Ethyl 7-Allylamino-2-(2-methoxy-2-propyl)-2H-pyrazolo[4,3-b]pyridine-6-carboxylate (D5)

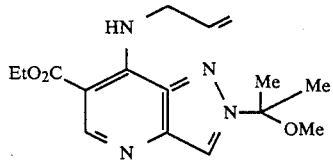

A mixture of ethyl 7-allylamino-1H-pyrazolo[4,3-b]pyridine-6-carboxylate (3.69 g, 15 mmol), 2,2-dimethoxypropane (9.2 ml, 75 mmol) and 4-toluenesulphonic acid (142 mg, 0.75 mmol) in acetone (200 ml) was heated under reflux for 48 h. The solution was cooled and stirred with solid potassium carbonate, then filtered and evaporated in vacuo. Column chromatography of the residue on basic alumina (100 g), eluting with ethyl acetate, gave the title compound as a white solid (3.07 g, 64%), m.p. 102°-103° C. Found: C, 60.31; H, 6.78; N, 17.60; C₁₆H₂₂N₄O₃ requires C, 60.36; H, 6.97; N, 17.60%

δ (CDCl₃):
1.40 (3H, t, J 7 Hz)
1.83 (6H, s)
3.08 (3H, s)
4.30 (2H, q, J 7 Hz)
4.73 (2H, t, J 6 Hz)
5.05–5.50 (2H, m)
5.70–6.30 (1H, m)
8.15 (1H, s)
8.73 (1H, s)
9.30 (1H, br s)

DESCRIPTION 6

7-Allylamino-6-hydroxymethyl-2-(2-methoxy-2-propyl)-2H-pyrazolo[4,3-b]pyridine (D6)

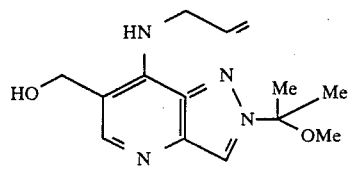

A solution of ethyl 7-allylamino-2-(2-methoxy-2-propyl)-2H-pyrazolo[4,3-b]pyridine-6-carboxylate (2.38 g, 7.5 mmol) in dry THF (tetrahydrofuran) (25 ml) was added dropwise to an ice-cooled suspension of lithium aluminium hydride (285 mg, 7.5 mmol) in dry THF (15 ml). The mixture was stirred at room temperature, under nitrogen, for 24 h, then water (0.3 ml), 10% sodium hydroxide solution (0.3 ml) and water (0.85 ml) were added sequentially. The mixture was filtered through Kieselguhr, the solvent was evaporated in vacuo, and the residual solid was recrystallised from ethyl acetate to give the title compound as needles (1.87 g, 90%), m.p. 152°–154° C. Found: C, 60.58; H, 7.21; N, 20.26 C₁₄H₂₀N₄O₂ requires C, 60.84; H, 7.29; N, 20.27%

δ (CDCl₃):
1.82 (6H, s)
3.00 (3H, s)
4.56 (2H, s)
4.67 (2H, t, J 6 Hz)
4.90–5.40 (3H, m)
5.65–6.30 (2H, m)
7.60 (1H, s)
8.00 (1H, s)

DESCRIPTION 7

Ethyl 2-(pyrazol-4-ylamino)cyclohexane-1-carboxylate (D7)

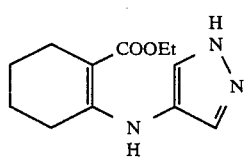

A solution of 4-nitropyrazole (5.2 g, 0.046 mole) in ethanol (150 ml) was hydrogenated over a 10% Pd/C catalyst (0.5 g) at atmospheric temperature and pressure until the uptake of hydrogen ceased. The catalyst was filtered off and the filtrate treated with ethyl 2-cyclohexanonecarboxylate (7.3 ml, 0.046 mole), before evaporating to dryness. A few drops of concentrated hydrochloric acid (0.1 ml) were added to the yellow oil, which was then heated on the steam bath under nitrogen for 10 minutes. The mixture was dissolved in ethyl acetate, washed with aqueous sodium hydrogen carbonate solution and water, then dried (MgSO₄) and concentrated to leave a yellow solid. This was recrystallised from ether/60°–80° petroleum ether to give the title compound as a white solid (9.7 g, 90%), m.p. 92°–94° C. Found: C, 61.20; H, 7.35; N, 18.00% C₁₂H₁₇N₃O₂ requires C, 61.25; H, 7.30; N, 17.85%

δ (CDCl₃):
1.25 (3H, t, J 7 Hz)
1.40–1.75 (4H, m)
2.00–2.40 (4H, m)
4.10 (2H, q, J 7 Hz)
7.30 (2H, s)
10.20 (1H, br s)
11.15 (1H, br s)

DESCRIPTION 8

4,5,6,7,8,9-Hexahydro-9-oxo-1H-pyrazolo[4,3-b]quinoline (D8)

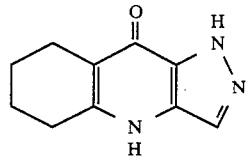

Ethyl 2-(pyrazol-4-ylamino)cyclohexene-1-carboxylate (8.5 g, 0.036 mole) was added rapidly to refluxing Dowtherm A (250 ml) under nitrogen and the mixture heated under reflux for a further 15 minutes, before allowing to cool to room temperature. The mixture was diluted with 60°–80° petroleum ether (200 ml) and the solid then filtered off, washed well with petroleum ether and then ethanol, before drying under vacuum to give the title compound as a white solid (6.26 g, 92%), m.p. >325° C. Found: C, 63.20; H, 5.85; N, 22.20% C₁₀H₁₁N₃O requires C, 63.50; H, 5.85; N, 22.20%

δ (CDCl₃/DMSO d₆):
1.50–1.90 (4H, m)
2.30–2.80 (4H, m)
7.60 (1H, s)
11.40 (1H, bs)

DESCRIPTION 9

9-Chloro-5,6,7,8-tetrahydro-1H-pyrazolo[4,3-b]quinoline (D9)

4,5,6,7,8,9-Hexahydro-9-oxo-1H-pyrazolo[4,3-b]quinoline (5.0 g, 0.026 mole) was treated with phosphoryl chloride (40 ml) and the mixture heated under reflux for 30 minutes. The excess reagent was evaporated off and the residue treated with water (30 ml) and then made basic by the addition of sodium carbonate solution. The solid was filtered off, washed with water, dried and recrystallised from ethyl acetate to give the title compound as a yellow solid (4.85 g, 88%), m.p.

190°–193° C. Found: C, 57.85; H, 4.95; N, 20.00; Cl, 16.95% C₁₀H₁₀ClN₃ requires C, 57.85; H, 4.85; N, 20.25; Cl, 17.20%

δ (CDCl₃/DMSO d₆):
1.70–2.00 (4H, m)
2.65–3.15 (4H, m)
8.00 (1H, s)

DESCRIPTION 10

Ethyl 2-(pyrazol-4-ylamino)cyclopentene-1-carboxylate (D10)

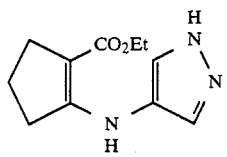

(D10)

The title compound was prepared from 4-nitropyrazole (5.2 g, 0.046 mole) as in description 7, using ethyl 2-cyclopentanonecarboxylate instead of ethyl 2-cyclohexanonecarboxylate. The product was obtained as a white solid (9.6 g, 94%) m.p. 121°–123° C.

δ (CDCl₃):
1.25 (3H, t, J=7 Hz)
1.60–2.00 (2H, m)
2.40–2.75 (4H, m)
4.15 (2H, q, J=7 Hz)
7.35 (2H, s)
8.80 (1H, br s)
11.40 (1H, br s)

DESCRIPTION 11

4,5,6,7,8-Pentahydro-8oxo-1H-cyclopenta[b]pyrazolo[3,4-e]pyridine (D11)

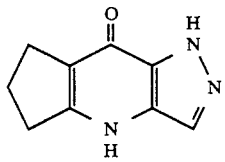

(D11)

The title compound was prepared from ethyl 2-(pyrazol-4-ylamino)cyclopentene-1-carboxylate (9.4 g, 0.042 mole) using the method of description 8. The product was obtained as a beige solid (6.2 g, 84%) m.p. >310° C.

δ (TFA)
1.95–2.50 (2H, m)
2.80–3.30 (4H, m)
8.20 (1H, s)

DESCRIPTION 12

8-Chloro-5,6,7-trihydro-1H-cyclopenta[b]pyrazolo[3,4-e]pyridine (D12)

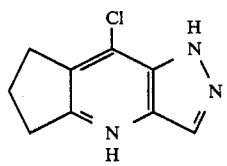

(D12)

The title compound was prepared from 4,5,6,7,8-pentahydro-8-oxo-1H-cyclopenta[b]pyrazolo[3,4-e]pyridine (6.0 g, 0.034 mole) using the method of description 9. The product was obtained as a white solid (5.9 g, 89%) m.p. 210°–213° C.

δ (CDCl₃/DMSO d₆):
1.90—2.40 (2H, m)
2.80–3.20 (4H, m)
8.00 (1H, s)

DESCRIPTION 13

Ethyl 2-acetyl-3-(4-pyrazolylamino)acrylate (D13)

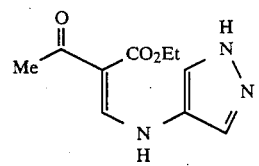

(D13)

A solution of 4-nitropyrazole (5.6 g, 50 mmol) in ethanol (200 ml) was hydrogenated over 10% palladium on charcoal (0.5 g) at room temperature and pressure for 3.5 h. The catalyst was filtered off and ethyl 2-acetyl-3-ethoxyacrylate (9.3 g, 50 mmol) was added to the solution under nitrogen. After 5 min, the solution was evaporated in vacuo and the residual solid was recrystallised from ethyl acetate/pentane (charcoal) to give the title compound (7.7 g, 69%), m.p. 126°–128° C. Found: C, 49.96; H, 6.28; N, 17.34%. C₁₀H₁₃N₃O₃.H₂O requires C, 49.78; H, 6.27; N, 17.41%.

δ (CDCl₃):
1.35 (3H, t, J=8 Hz)
2.55 (3H, s)
4.20 (2H, q, J=8 Hz)
7.65 (2H, s)
8.25 (1H, d, J=12 Hz)
12.55 (1H, br d, exchanges with D₂O)

DESCRIPTION 14

6-Acetyl-4,7-dihydro-7-oxo-1H-pyrazolo[4,3-b]pyridine (D14)

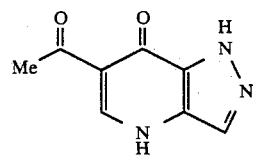

(D14)

Ethyl 2-acetyl-3-(4-pyrazolylamino)acrylate (D13, 1.0 g, 4.5 mmol) was added to boiling Dowtherm A, and the solution was heated under reflux for 20 min. The mixture was allowed to cool and 60°–80° petroleum ether (100 ml) was added. The solid was filtered off and washed well with petroleum ether to give the title compound (590 mg, 74%), m.p. >320° C.

δ (TFA):
2.95 (3H, s)
8.80 (1H, s)
9.45 (1H, s)
M⁺, Found: 177.0530, C₈H₇N₃O₂ requires 177.0538.

DESCRIPTION 15

6-Acetyl-7-chloro-1H-pyrazolo[4,3-b]pyridine (D15)

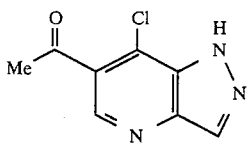
(D15)

A mixture of 6-acetyl-4,7-dihydro-7-oxo-1H-pyrazolo-[4,3-b]pyridine (D14, 1.6 g, 9 mmol) and phosphorus oxychloride (15 ml) was heated at 80° C. for 30 min. Excess reagent was removed in vacuo, water was added and the mixture was adjusted to pH 9 with 10% sodium carbonate solution. The resulting mixture was extracted with ethyl acetate (4×50 ml), and the extracts were washed with brine, dried (MgSO$_4$) and evaporated in vacuo to leave the title compound as a yellow solid, which was used without purification.

δ (CDCl$_3$):
2.75 (3H, s)
8.25 (1H, s)
8.70 (1H, s)

EXAMPLE 1

7n-Butylamino-6-methyl-1H-pyrazolo[4,3-b]pyridine (E1)

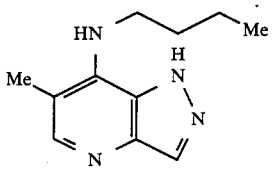
(E1)

Ethyl 7-chloro-1H-pyrazolo[4,3-b]pyridine-6-carboxylate (3.5 g, 15.5 mmol) was dissolved in n-butylamine (25 ml) and stirred at room temperature for 3 h. Excess butylamine was removed in vacuo and the residual solid was washed well with water, and recrystallised from ethyl acetate to give ethyl 7-n-butylamino-1H-pyrazolo [4,3-b]pyridine-6-carboxylate (2.75 g, 67%), m.p. 164°-170° C.

A solution of ethyl 7-n-butylamino-1H-pyrazolo[4,3-b]-pyridine-6-carboxylate (524 mg, 2 mmol) in dry THF (15 ml) was added dropwise to a stirred suspension of lithium aluminium hydride (152 mg, 4 mmol) in THF (15 ml). The mixture was heated under reflux under nitrogen for 90 min then cooled. Ether (30 ml), water (0.15 ml), 10% sodium hydroxide solution (0.15 ml) and water (0.45 ml) were added sequentially, with stirring, and the mixture was filtered, then evaporated in vacuo. The glassy residue (300 mg) was recrystallised from ethyl acetate/ether, to give a white solid, m.p. 86°-95° C.

δ (CDCl$_3$):
0.95 (3H, t, J=7 Hz)
1.15–2.0 (4H, m)
2.25 (3H, s)
3.80 (2H, t, J=7 Hz)
7.90 (1H, br s, exchanges with D$_2$O)
8.12 (1H, s)
8.17 (1H, s)

EXAMPLE 2

7-Allylamino-6-cyano-1H-pyrazolo[4,3-b]pyridine (E2)

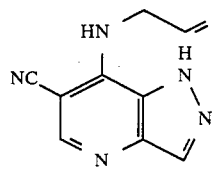
(E2)

Trifluoroacetic anhydride (1.91 ml, 13.5 mmol) was added dropwise to an ice-cooled, stirred suspension of 7-allylamino-1H-[4,3-b]pyridine-6-carboxamide (1.4 g, 6.45 mmol) in dry dioxane (10 ml) and pyridine (1.6 ml, 19.3 mmol). The mixture was stirred at room temperature overnight, water was added and the pH was adjusted to pH 9 with 10% sodium carbonate solution. The solid was filtered off, and the aqueous solution was extracted with ethyl acetate. The extracts were washed with brine, dried (MgSO$_4$) and evaporated in vacuo. The residue was crystallised from ethanol/ethyl acetate to give the title compound (260 mg, 20%), m.p. 249°-252° C.

δ (DMSO d$_6$):
4.55 (2H, m)
5.10–5.35 (2H, m)
5.80–6.30 (1H, m)
7.90 (1H, br s)
8.20 (1H, s)
8.40 (1H, s)

EXAMPLE 3

7-Allylamino-6-hydroxymethyl-2-methyl-2H-pyrazolo[4,3-b]pyridine (E3)

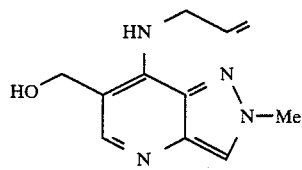
(E3)

A solution of ethyl 7-allylamino-2-methyl-2H-pyrazolo-[4,3-b]pyridine-6-carboxylate (100 mg, 0.38 mmol) in dry THF (2 ml) was added dropwise to an ice-cooled suspension of lithium aluminium hydride (15 mg, 0.39 mmol) in THF (1 ml). The mixture was stirred at room temperature, under nitrogen, for 16 h, then water (0.03 ml), 10% sodium hydroxide solution (0.4 ml) and water (0.09 ml) were added sequentially. The solids were filtered off and washed with ethyl acetate. The solution was evaporated in vacuo to give a solid, which was recrystallised from ethyl acetate to give the title compound as needles (40 mg, 48%), m.p. 151°-159° C.

δ (DMSO d$_6$):
4.10 (3H, s)
4.52 (2H, s)
4.50–4.70 (2H, m)
4.90–5.35 (2H, m)
5.70–6.10 (1H, m)
6.30 (1H, m)
7.90 (1H, s)
8.17 (1H, s)

EXAMPLE 4

7-Allylamino-6-hydroxymethyl-1H-pyrazolo[4,3-b]pyridine

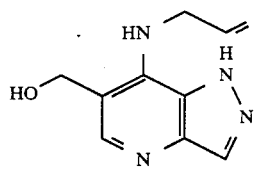
(E4)

7-Allylamino-6-hydroxymethyl-2-(2-methoxy-2-propyl)-2H-pyrazolo[4,3-b]pyridine (1.30 g, 4.7 mmol) was suspended in water (15 ml) and made acidic with 6N hydrochloric acid. After 45 min the solution was adjusted to pH 9 with 10% sodium carbonate solution. The precipitated solid was filtered off and dried to give the title compound (0.89 g, 93%), m.p. 190°–192° C. Found: C, 58.58; H, 5.62; N, 27.25 $C_{10}H_{12}N_4O$ requires C, 58.81; H, 5.92; N, 27.43%

δ (DMSO $d_6$):
4.35 (2H, t, J 6 Hz)
4.57 (2H, s)
4.95–5.20 (2H, m)
5.30 (1H, s)
5.70–6.30 (2H, m)
8.05 (1H, s)
8.10 (1H, s)

EXAMPLE 5

9-(2-Hydroxyethylamino)-5,6,7,8-tetrahydro-1H-pyrazolo-[4,3-b]quinoline (E5)

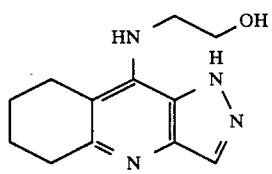
(E5)

9-Chloro-5,6,7,8-tetrahydro-1H-pyrazolo[4,3-b]quinoline (2.45 g, 0.012 mole) and ethanolamine (2.2 ml, 0.036 mole) were heated under reflux in dry xylene (25 ml) for 24 hours. The solvent was evaporated off and the residue dissolved in water/methanol. The pH of the solution was adjusted to 9 by the addition of 10% sodium carbonate solution. The precipitate which formed was filtered off, washed with water, dried and recrystallised from ethyl acetate to give the title compound as a beige solid (0.55 g, 20%), m.p. 205°–210° C. Found: C, 62.05; H, 6.95; N, 24.00% $C_{12}H_{16}N_4O$ requires C, 62.05; H, 6.95; N, 24.10%

δ (DMSO $d_6$):
1.60–1.90 (4H, m)
2.40–2.90 (4H, m)
3.50–3.90 (4H, m)
5.35–5.60 (1H, m)
8.00 (1H, s)

EXAMPLE 6

9-Isobutylamino-5,6,7,8-tetrahydro-1H-pyrazolo[4,3-b]quinoline (E6)

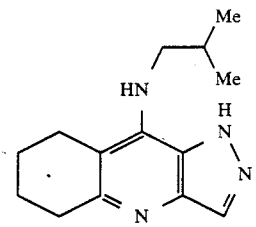
(E6)

9-Chloro-5,6,7,8-tetrahydro-1H-pyrazolo[4,3-b]quinoline (4.90 g, 0.024 mole) and isobutylamine (11.7 ml, 0.118 mole) were heated under reflux under nitrogen in dry xylene (50 ml) for 6 days. The solution was concentrated to dryness, the residue dissolved in water/methanol and the solution adjusted to pH 9–10 by addition of 10% sodium carbonate solution. The precipitate was filtered of, washed with water, dried and recrystallised from ethyl acetate to give the title compound as a beige solid (0.85 g, 15%), m.p. 124°–127° C. Found: C, 68.45; H, 8.55; N, 22.80%. $C_{14}H_{20}N_4$ requires C, 68.80; H, 8.25; N, 22.95%.

δ ($CDCl_3$):
1.05 (6H, d, J=8 Hz)
1.85–2.00 (5H, m)
2.50–2.55 (2H, m)
2.95–3.00 (2H, m)
3.55–3.60 (2H, m)
4.10–4.20 (1H, m)
8.06 (1H, s)
Observed mass=244.1688. $C_{14}H_{20}N_4$ requires 244.1681.

EXAMPLE 7

8-(2-Hydroxyethylamino)-5,6,7-trihydro-1H-cyclopenta[b]pyrazolo[3,4-e]pyridine (E7)

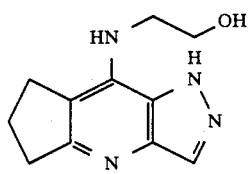
(E7)

The title compound was prepared from 8-chloro-5,6,7-trihydro-1H-cyclopenta[b]pyrazolo[3,4-e]pyridine (3.0 g, 0.016 mole) using the method of example 5. The product was recrystallised from ethyl acetate/methanol to give a beige solid (1.27 g, 38%) m.p. 232°–235° C.

δ (DMSO $d_6$):
1.90–2.10 (2H, m)
2.70–2.95 (4H, m)
3.50–3.75 (4H, m)
5.80–5.95 (1H, m)
7.90 (1H, s)
12.75 (1H, br s)
Observed mass=218.1168. $C_{11}H_{14}N_4O$ requires 218.1159.

EXAMPLE 8

8-Isobutylamino-5,6,7-trihydro-1H-cyclopenta[b]pyrazolo[3,4-e]pyridine (E8)

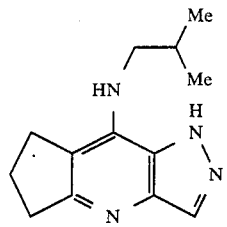
(E8)

A solution of 8-chloro-5,6,7-trihydro-1H-cyclopenta[b]pyrazolo[3,4-e]pyridine (2.70 g, 0.014 mole) and isobutylamine (17 ml, 0.17 mole) in dry xylene (90 ml) was heated in a pressure vessel at 150° C. and 30 psi for 44 h and then at 175° C. and 40 psi for a further 45 h. The solution was evaporated to dryness and the residue dissolved in water/methanol. The pH of the solution was adjusted to 9-10 by addition of 10% sodium carbonate solution and then extracted with chloroform. The organic extract was washed with brine, dried (MgSO$_4$) and evaporated to dryness. The product was purified by column chromatography on basic alumina eluting with 20% methanol/ethyl acetate. The title compound was obtained as a beige solid after recrystallisation from ethyl acetate (1.20 g, 37%) m.p. 148°-150° C.

δ (CDCl$_3$):
0.92 (3H, d, J=8 Hz)
1.60-2.00 (1H, m)
2.00-2.35 (2H, m)
2.80-3.15 (4H, m)
3.30-3.55 (2H, m)
5.35-5.60 (1H, m)
8.00 (1H, s)
10.00 (1H, br s)

Observed mass=230.1532. C$_{13}$H$_{18}$N$_4$ requires 230.1523.

EXAMPLE 9

6-Aminomethyl-7-propylamino-1H-pyrazolo[4,3-b]pyridine (E9)

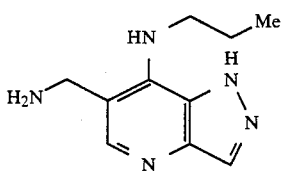
(E9)

A solution of 7-allylamino-6-cyano-1H-pyrazolo[4,3-b]pyridine (E2, 487 mg, 2.4 mmol) in ethanol (100 ml) and ethanolic hydrogen chloride (2 ml) was hydrogenated over 10% palladium on charcoal (200 mg) at 40° C. and atmospheric pressure for 48 h. The catalyst was filtered off and the solution was evaporated in vacuo. The resulting solid was dissolved in water (15 ml) and the solution was adjusted to pH 8 with 10% sodium carbonate solution. After washing with ethyl acetate, the aqueous solution was cooled at 4° C. for 2 days. A white solid separated and was filtered off and dried to give the title compound (185 mg, 37%), m.p. 97°-100° C.

δ (DMSO d$_6$):
1.0 (3H, t, J=6 Hz)
1.65 (2H, m)
3.7 (2H, t, J=7 Hz)
3.8-4.3 (3H, m)
6.85 (½H, br s, exchanges with D$_2$O)
7.4 (½H, br s, exchanges with D$_2$O)
7.95 (1H, s)
8.1 (1H, s)
M+, Found: 205.1323. C$_{10}$H$_{15}$N$_5$ requires 205.1327.

EXAMPLE 10

6-Acetyl-7-allylamino-1H-pyrazolo[4,3-b]pyridine (E10)

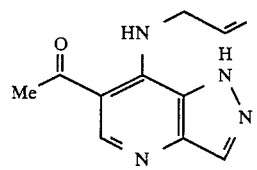
(E10)

A solution of 6-acetyl-7-chloro-1H-pyrazolo[4,3-b]pyridine (D15, 340 mg, 1.7 mmol) in allylamine (5 ml) was stirred at room temperature for 16 h. Excess allylamine was removed in vacuo and the residue was dissolved in aqueous methanol. The solution was adjusted to pH 8 with 10% sodium carbonate solution, and extracted with ethyl acetate (4×50 ml). The extracts were washed with brine (50 ml), dried (MgSO$_4$) and evaporated in vacuo to give a sticky solid. This was crystallised from ethyl acetate/ethanol to give the title compound (280 mg, 75%), m.p. 211°-213° C. Found: C, 60.49; H, 5.81; N, 25.55. C$_{11}$H$_{12}$N$_4$O requires C, 61.10; H, 5.59; N, 25.91%.

δ (CDCl$_3$):
2.70 (3H, s)
4.70 (2H, m)
5.2-5.55 (2H, m)
5.85-6.40 (1H, m)
6.95 (1H, br s)
8.25 (1H, s)
8.85 (1H, s)

PHARMACOLOGICAL DATA

Illustrative compounds of the invention were tested in various relevant disease models as follows:

(1) MOUSE CANTHARIDIN SCREEN

Compounds were tested for topical anti-inflammatory activity in a cantharidin mouse ear screen, modified from Swingle, K. F., Reiter, M. J. and Schwartzmiller, D. H., Arch. Int. Pharmacodyn., (1981), 254, 168-176).

(a) 25 μg cantharidin (in 10 μl THF/MeOH) was applied to both ears. Compound, in the same solvent, was applied at the same time, to the left ear only. Ears were weighed 24 h after cantharidin application. Percentage inhibition of the acute inflammatory swelling refers to the increase in weight of left ears (cantharidine plus compound) compared with solvent-treated negative controls, as a proportion of the increase in weight of right ears (cantharidin alone) over similar controls.

| COMPOUND EXAMPLE NO. | DOSE (μg/ear) | % INHIBITION |
| --- | --- | --- |
| 1 | 500 | 95*** |
| 5 | 500 | 91*** |
| 6 | 500 | 97*** |
| 8 | 500 | 97*** |
| 9 | 500 | 91*** |

***$p < 0.001$

(2) CARRAGEENIN-INDUCED PLEURISY IN THE RAT

This model of monocyte accumulation is based on the method of R. Vinegar, J. F. Truax, J. L. Selph and F. A. Voelker [Federation Proceedings 41, 2588–2595, 1982].

0.2 ml of a 2.0% solution of λ-carrageenin (Viscarin 402) in saline was injected intrapleurally in anaesthetised rats (wt. approx. 175–200 g). Compounds were administered 1 hour before carrageenin and at 24 and 48 hours after carrageenin. 72 hours after carrageenin injection, 4.0 ml of EDTA solution (5 g EDTA in 100 ml of 0.9% saline and 325 mg phenol red added together with saline to 1 liter) was injected intrapleurally after killing the animals, and the exudate was removed with a syringe through the diaphragm. Exudate volume was calculated from the dilution of the phenol red injected, determined spectrophotometrically (560 nm) and cellular content estimated with a DNA assay [Karsten U. and Wollenberger A. Anal. Biochem. 77, 464–470, 1977].

The Compound of Example 5 at a dose of 25 mg/kg p.o. gave a 31% inhibition of DNA content and a 36% inhibition of exudate volume compared to control levels ($p<0.05$).

(3) MOUSE OXAZOLONE SCREEN

Compounds were tested for topical anti-inflammatory activity in a screen using the mouse sensitized to oxazolone, by a method modified from that of Dietrich and Hess [Int. Arch. Allergy, 38, 246 (1970)].

Mice were sensitized with oxazolone (2 mg in 20 μl EtOH) on a shaved area of the abdomen. 5 days later, the animals received 10 μl THF/MeOH (1:1 v/v) on the right ear and the test compound in the same solvent on the left ear. 1 hour later, the animals were challenged with 100 μg oxazolone in 10 μl acetone on each ear. Ear weights were measured 24 hours later. Percentage inhibition of the inflammatory swelling refers to the increase in weight of left ears (oxazolone plus compound in THF/MeOH) compared to untreated negative controls, as a proportion of the increase in weight of right ears (oxazolone only in THF/MeOH) over similar controls.

| COMPOUND EXAMPLE NO. | DOSE (μg/ear) | % INHIBITION |
| --- | --- | --- |
| 6 | 200 | 66*** |
| 8 | 200 | 49** |

**$p < 0.01$;
***$p < 0.001$

In the tests reported above, no toxic effects were observed for the compounds illustrated.

We claim:

1. A compound of the formula (I):

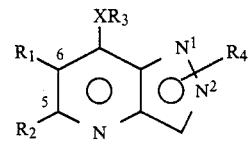

wherein:

X is NR wherein R is hydrogen or $C_{1-6}$ alkyl; oxygen; sulphur; SO; or $SO_2$; or R and $R_3$ taken together are $C_{4-6}$ polymethylene;

$R_1$ is hydrogen or $C_{1-6}$ alkyl; and $R_2$ is CN, $CR_5R_6Y$ where $R_5$ and $R_6$ are independently selected from hydrogen and $C_{1-4}$ alkyl and Y is selected from hydrogen, $OR_7$, $SR_7$, where $R_7$, is hydrogen, $C_{1-4}$ alkyl, or $C_{2-4}$ alkanoyl, and $NR_8R_9$ where $R_8$ and $R_9$ are independently hydrogen, $C_{1-4}$ alkyl, $C_{2-4}$ alkenyl or $C_{2-4}$ alkanoyl or $R_8$ and $R_9$ together are $C_{4-6}$ polymethylene, or $R_2$ is $COR_{10}$ where $R_{10}$ is $C_{1-4}$ alkyl, or $R_2$ is hydrogen, $C_{1-6}$ alkyl or phenyl optionally substituted by halogen, $CF_3$, $C_{1-4}$ alkoxy or $C_{1-4}$ alkyl; and $R_1$ is CN, $CR_5R_6Y$ or $COR_{10}$ as defined for $R_2$ above, provided that one of $R_1$ and $R_2$ is not hydrogen when the other is $C_{1-6}$ alkyl, or $R_1$ and $R_2$ are not both $C_{1-6}$ alkyl; or $R_1$ and $R_2$ together form $C_3-C_6$ polymethylene optionally substituted by $C_1-C_4$ alkyl;

$R_3$ is $C_{1-10}$ alkyl or $C_{3-10}$ cycloalkyl, either optionally substituted by hydroxy, $C_{1-4}$ alkoxy, thiol, $C_{1-4}$ alkylthio or $NR_{11}R_{12}$ wherein $R_{11}$ and $R_{12}$ are independently hydrogen, $C_{1-6}$ alkyl or $C_{2-7}$ alkanoyl or together are $C_{3-6}$ polymethylene; $C_{2-10}$ alkenyl; or phenyl optionally substituted by one or two of halogen; $CF_3$, $C_{1-4}$ alkoxy, $C_{1-4}$ alkyl, hydroxy, nitro, cyano, $C_{2-10}$, acyloxy, $NR_{13}R_{14}$ wherein $R_{13}$ and $R_{14}$ are independently selected from hydrogen, $C_{1-6}$ alkyl, $C_{2-7}$ alkanoyl or $C_{1-6}$ alkylsulphonyl or $COR_{15}$ wherein $R_{15}$ is hydroxy, $C_{1-6}$ alkoxy or $NR_6R_{17}$ wherein $R_{16}$ and $R_{17}$ are independently selected from hydrogen or $C_{1-6}$ alkyl; or together with R is $C_{4-6}$ polymethylene; and $R_4$ is hydrogen; or $C_{1-4}$ alkyl or benzyl optionally substituted in the phenyl ring by one or two of halogen, $CF_3$, $C_{1-4}$ alkoxy or $C_{1-4}$ alkyl and is attached at nitrogen atom 1 or 2.

2. A compound according to claim 1 wherein $R_1$ is selected from the group consisting of hydrogen and $C_{1-6}$ alkyl; and $R_2$ is selected from the group consisting of CN, $CR_5R_6Y'$ wherein $Y'$ is $OR_7$, $SR_7$ or $NR_8R_9$, and $COR_{10}$, wherein $R_5$, $R_6$, $R_7$, $R_8$, $R_9$ and $R_{10}$ are as defined in claim 1.

3. A compound according to claim 1 of formula (VI):

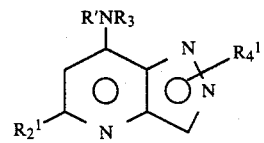

wherein $R_2{}^1$ is CN, $CR_5R_6Y'$ or $COR_{10}$ wherein $R_5$, $R_6$ and $R_{10}$ are as defined in claim 1, $R'$ is hydrogen or methyl, $R_3$ is as defined in claim 1, $R_4$ is hydrogen or 2-methyl, and $Y'$ is $OR_7$, $SR_7$ or $NR_8R_9$ wherein $R_7$, $R_8$ and $R_9$ are as defined in claim 1.

4. A compound according to claim 3 of formula (VII):

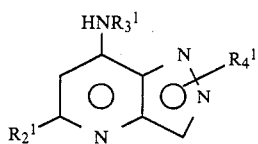

wherein $R_3^1$ is n-butyl, iso-butyl, allyl, 2-hydroxyethyl, 3-dimethylaminopropyl or 3-diethylaminopropyl; and $R_2^1$ is as defined in claim 3.

5. A compound according to claim 1 of formula (XI):

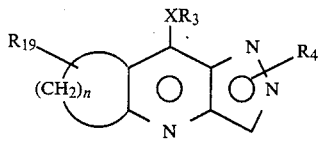

in which n is 3 to 6 and $R_{19}$ is hydrogen or $C_1$–$C_4$ alkyl, and X, $R_3$ and $R_4$ are as defined in claim 1.

6. A compound according to claim 5 of formula (X):

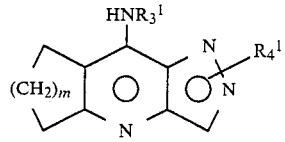

in which $R_3^1$ is n-butyl, iso-butyl, allyl, 2-hydroxyethyl, 3-dimethylaminopropyl or 3-diethylaminopropyl; m is 1 or 2.

7. A compound according to claim 1, which is selected from the group consisting of:
  7-Allylamino-6-cyano-1H-pyrazolo[4,3-b]pyridine,
  7-Allylamino-6-hydroxymethyl-2-methyl-2H-pyrazolo[4,3-b]pyridine,
  7-Allylamino-6-hydroxymethyl-1H-pyrazolo[4,3-b]pyridine,
  9-(2-Hydroxyethylamino)-5,6,7,8-tetrahydro-1H-pyrazolo[4,3-b]quinoline,
  9-Isobutylamino-5,6,7,8-tetrahydro-1H-pyrazolo[4,3-b]quinoline,
  8-(2-Hydroxyethylamino)-5,6,7-trihydro-1H-cyclopenta[b]pyrazolo[3,4-e]pyridine,
  8-Isobutylamino-5,6,7-trihydro-1H-cyclopenta[b]pyrazolo[3,4-e]pyridine,
  6-Aminomethyl-7-propylamino-1H-pyrazolo[4,3-b]pyridine, and
  6-Acetyl-7-allylamino-1H-pyrazolo[4,3-b]pyridine.

8. A pharmaceutically acceptable salt or solvate of a compound according to claim 1.

9. A pharmaceutical composition for use in treating inflammatory, rheumatic or allergic disorders comprising an antiinflammatory, antirheumatic or antiallergic effective amount of a compound according to claim 1 and a pharmaceutically acceptable carrier.

* * * * *